United States Patent
Ni et al.

(10) Patent No.: US 12,070,501 B1
(45) Date of Patent: Aug. 27, 2024

(54) TOPICAL OPHTHALMOLOGICAL COMPOSITIONS

(71) Applicant: ADS Therapeutics LLC, Irvine, CA (US)

(72) Inventors: Jinsong Ni, Irvine, CA (US); Van Dinh, Irvine, CA (US); Rong Yang, Irvine, CA (US)

(73) Assignee: ADS Therapeutics LLC, Irvine, CA (US)

( * ) Notice: Subject to any disclaimer, the term of this patent is extended or adjusted under 35 U.S.C. 154(b) by 0 days.

(21) Appl. No.: 17/976,660

(22) Filed: Oct. 28, 2022

Related U.S. Application Data

(63) Continuation of application No. PCT/US2022/014811, filed on Feb. 2, 2022.

(60) Provisional application No. 63/145,091, filed on Feb. 3, 2021.

(51) Int. Cl.
| | | |
|---|---|---|
| *A01N 43/00* | (2006.01) | |
| *A01N 43/46* | (2006.01) | |
| *A61K 9/00* | (2006.01) | |
| *A61K 31/46* | (2006.01) | |
| *A61K 31/55* | (2006.01) | |
| *A61K 47/06* | (2006.01) | |
| *A61K 47/14* | (2017.01) | |
| *A61P 27/10* | (2006.01) | |

(52) U.S. Cl.
CPC ............ *A61K 47/14* (2013.01); *A61K 9/0048* (2013.01); *A61K 31/46* (2013.01); *A61K 47/06* (2013.01); *A61P 27/10* (2018.01)

(58) Field of Classification Search
None
See application file for complete search history.

(56) References Cited

U.S. PATENT DOCUMENTS

| | | |
|---|---|---|
| 2007/0254914 A1 | 11/2007 | Wu et al. |
| 2019/0328717 A1 | 10/2019 | Gunther et al. |
| 2019/0343793 A1 | 11/2019 | Gunther et al. |
| 2019/0343848 A1 | 11/2019 | Rigas |
| 2020/0188318 A1 | 6/2020 | Günther et al. |
| 2020/0268682 A1 | 8/2020 | Gunther et al. |
| 2023/0355594 A1 | 11/2023 | Ni et al. |

FOREIGN PATENT DOCUMENTS

| | | |
|---|---|---|
| CN | 101049287 | 10/2007 |
| WO | WO 1997/012852 | 4/1997 |
| WO | WO 2001097774 | 12/2001 |
| WO | WO 2012/062834 | 5/2012 |
| WO | WO 2012/161655 | 11/2012 |
| WO | WO 2014/041055 | 3/2014 |
| WO | WO 2014/041071 | 3/2014 |
| WO | WO 2016/172712 | 10/2016 |
| WO | WO 2018/154440 | 8/2018 |
| WO | WO 2018/228975 | 12/2018 |
| WO | WO 2020074697 | 4/2020 |
| WO | WO 2020152046 | 7/2020 |
| WO | WO 2022076852 | 4/2022 |

OTHER PUBLICATIONS

Carr et al., "Myopia-Inhibiting Concentrations of Muscarinic Receptor Antagonists Block Activation of Alpha 2A-Adrenoceptors In Vitro", Physiology and Pharmacology, vol. 59, Nr.:7, pp. 2778-2791 (Jun. 1, 2018).
Arumugam et al., "Muscarinic Antagonist Control of Myopia: Evidence for M 4 and M 1 Receptor-Based Pathways in the Inhibition of Experimentally-Induced Axial Myopia in the Tree Shrew", Investigative Opthalmology & Visual Science, vol. 53, Nr.:9, pp. 5827-5837 (Aug. 24, 2012).
Holland, E.: "Semifluorinated alkane technology brings advantages for topical therapy.", Ophthalmology Times, Nov. 15, 2020, Retrieved Apr. 21, 2022, from the Internet <URL:https://www.ophthalmologytimes.com/view/semifluorinated-alkane-technology-brings-advantages-topical-therapy>.
Berton et al., "Stability of ophthalmic atropine solutions for child myopia control," Pharmaceutics, Aug. 2020, 12(8):E781, 17 pages.
Cho et al., "Rates of Alkaline Hydrolysis and Muscarinic Activity of Some Aminoacetates and Their Quaternary Ammonium Analogs," J. of Medicinal Chem., 1972, 15, 391-394.
Cooper et al., "A review of current concepts of the etiology and treatment of myopia," Eye & Contact Lens, Jul. 2018, 44(4):231-247.
Grzybowski et al "A Review of Pharmacological Presbyopia Treatment," Asia-Pacific Journal of Ophthalmology, 2020, 9, 226-233.
International Preliminary Report on Patentability International Appln. No. PCT/US2021/054221, mailed on Apr. 20, 2023, 7 pages.
International Preliminary Report on Patentability International Appln. No. PCT/US2022/014811, mailed on Aug. 17, 2023, 7 pages.
International Search Report and Written Opinion in International Appln. No. PCT/US2021/054221, mailed on Jan. 21, 2022, 8 pages.
International Search Report and Written Opinion in International Appln. No. PCT/US2022/014811, mailed on Jun. 3, 2022, 9 pages.
Li et al., "Low-concentration atropine eye drops for myopia progression," Asia-Pacific Journal of Ophthalmology, Sep./Oct. 2019, 8(5):360-365.
Romano, "Double-blind cross-over comparison of aceclidine and pilocarpine in open-angle glaucoma", Brit. J. Ophthal., 1970 54, 510-521.
Saito et al., "Physical, chemical, and microbiological stability study of diluted atropine eye drops," Journal of Pharmaceutical health Care and Sciences, Dec. 2019, 5(25): 1-6.
Wang et al., "The penetration and distribution of topical atropine in animal ocular tissues," Acta Pharmacologica, 2019, 97:e238-e247, 10 pages.
Wu et al., "Update in myopia and treatment strategy of atropine use in myopia control," Eye, Jan. 2019, 33(1):3-13.

(Continued)

*Primary Examiner* — Layla Soroush
(74) *Attorney, Agent, or Firm* — Fish & Richardson P.C.

(57) ABSTRACT

A topical ophthalmological composition includes a muscarinic receptor antagonist as an active pharmaceutical ingredient; and medium chain triglycerides (MCTs) or light liquid paraffin oil as liquid vehicle. The topical ophthalmological composition treats an ocular disease.

15 Claims, 2 Drawing Sheets

(56) References Cited

OTHER PUBLICATIONS

Yam et al., "Two-year clinical trial of the low-concentration atropine for myopia progression (LAMP) study: Phase 2 report," Ophthalmology, Jul. 2020, 127(7):910-919.

Zhu et al., "Aceclidine and pilocarpine interact differently with muscarinic receptor in isolated rabbit iris muscle," Life Sciences, Feb. 2006, 78(14):1617-1623.

TOPICAL OPHTHALMOLOGICAL COMPOSITIONS

This application is a Continuation Application of PCT/US2022/014811, filed on Feb. 2, 2022, which claims priority to U.S. Provisional Patent Application No. 63/145,091, filed on Feb. 3, 2021, which is incorporated by reference for all purposes as if fully set forth herein.

FIELD OF THE INVENTION

The present invention relates to topical ophthalmological compositions of a muscarinic receptor antagonist dissolved in medium chain triglycerides (MCTs) or light liquid paraffin oil as liquid vehicle, wherein, the formulation of atropine is used for treating myopia.

BACKGROUND OF THE INVENTION

Atropine is an anti-muscarinic compound and is a competitive antagonist of muscarinic receptors. It has anti-parasympathetic functions. It is used for several indications such as anticholinergic poisoning and bradycardia. In the eye, it is traditionally used for dilating pupil. Recently, low dose of atropine is shown be able to attenuate the progression of myopia in young adults (Li 2019). For the myopia indication, atropine is approved in only a few countries as of now.

Myopia, or nearsightedness, is a condition in which people can see close objects clearly, but objects farther away appear blurred. Myopia occurs if the eyeball is too long or the cornea (the clear front cover of the eye) is too curved so that distant objects can't be focused correctly on retina. Myopia is the most common eye disorder worldwide. About 30 percent of the U.S. population has myopia. The etiology of myopia is unknown. Genetics is believed to have a role in myopia. Myopia development may be affected by how a person uses the eyes. It may occur in school-age children and progresses until about age 20. However, myopia may also develop in adults due to visual stress or health conditions such as diabetes. Myopia may increase the risk of other ocular diseases (Wu 2019).

Atropine solution (water-based) formulations have been tested in multiple clinical trials and is proven to be able to slow down the progression of myopia (Cooper 2018, Li 2019, Yam 2020). In the water-based formulation, atropine is prone to degradation at neutral pH solution once the container is open to the air, therefore, the shelf life of the product at neutral pH is often less than 1 year. Low pH of 3-6 in the formulation is used to increase the stability of atropine in solution (Berton 2020; Saito 2019). However, low pH is also known to cause irritation and discomfort in the eye.

This invention uses an organic liquid carrier to create a more stable and less irritating formulation of atropine for ocular, in particular myopia, indications.

In addition, atropine solution was used for causing cycloplegic refraction in the eye of the subject, for causing mydriasis in the eye of the subject, for treating amblyopia or lazy eye in children, for relieving vitreous floater symptoms, for treating or preventing painful ciliary muscle spasm or for treating myopia progression in pediatric subjects.

SUMMARY OF THE INVENTION

In one embodiment, the present invention provides a topical ophthalmological composition. The topical ophthalmological composition includes a muscarinic receptor antagonist as an active pharmaceutical ingredient (API); and a liquid vehicle selected from the group consisting of a medium chain triglyceride (MCT) and a light liquid paraffin oil.

The topical ophthalmological composition treats an ocular disease.

In another embodiment, the muscarinic receptor antagonist is selected from the group consisting of atropine, pirenzepine, aclidinium bromide, benztropine, cyclopentolate, diphenhydramine, doxylamine, dimenhydrinate, dicyclomine, darifenacin, flavoxate, hydroxyzine, ipratropium, mebeverine, oxybutynin, procyclidine, scopolamine, solifenacin, tropicamide, tiotropium, trihexyphenidyl, and tolterodine.

In another embodiment, the muscarinic receptor antagonist is atropine.

In another embodiment, the atropine is in a free base form or a salt form.

In another embodiment, a concentration of the atropine in the free base form is from about 0.001% to about 0.1% (w/w).

In another embodiment, the atropine free base is formulated in the MCT or formulated in the light liquid paraffin.

In another embodiment, the MCT is a triglyceride of fatty acids, and the fatty acids selected from the group consisting of hexanoic acid, octanoic acid, decanoic acid, and dodecanoic acid.

In another embodiment, the topical ophthalmological composition further includes a semi-fluorinated alkane compound. The semi-fluorinated alkane compound has a formula of RFRH or a formula of RFRHRF; RF is a perfluorinated hydrocarbon with 1 to 15 carbon atoms, and wherein RH is a non-fluorinated hydrocarbon with 1 to 15 carbon atoms.

In another embodiment, a weight ratio of the MCT or the light liquid paraffin oil to the semi-fluorinated alkane is from 99 to 1.

In another embodiment, the semifluorinated alkane is selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10).

In another embodiment, the semifluorinated alkane is F6H8 (perfluorohexyloctane).

In another embodiment, the topical ophthalmological composition further includes an organic cosolvent. The organic cosolvent is selected from the group consisting of phenethyl alcohol, ethanol, isopropanol, glycerol, propylene glycol, and polyethylene glycol.

In another embodiment, the organic cosolvent is phenethyl alcohol.

In another embodiment, a concentration of phenethyl alcohol is about 0.01% to about 1% (w/w).

In another embodiment, the topical ophthalmological composition is a non-aqueous solution, a suspension, or an emulsion.

In another embodiment, the atropine in the topical ophthalmological composition is chemically stable for at least 0.5 year, for at least 1 year, or for at least 2 year.

In another embodiment, the topical ophthalmological composition is adapted for topically administering as an eye drop to an eye of a patient.

In another embodiment, the topical ophthalmological composition causes minimal irritation in the eye.

In another embodiment, the ocular disease is myopia.

In another embodiment, the topical ophthalmological composition slows a myopia progression.

In another embodiment, a topical ophthalmological composition is provided, comprising about 0.001% to about 0.1% (w/w) atropine as an active pharmaceutical ingredient (API); a medium chain triglyceride (MCT) liquid vehicle; and a semi-fluorinated alkane compound selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10).

In this and other embodiments, the MCT can be present in a concentration of from about 10% to about 70%. The MCT can be a triglyceride of fatty acids selected from the group consisting of hexanoic acid, octanoic acid, decanoic acid, and dodecanoic acid. The MCT is present in a concentration of about 10% and the semi-fluorinated alkane compound is present in a concentration of about 90%. The MCT can comprise octanoic acid, decanoic acid, or a combination thereof. The semi-fluorinated alkane compound can be present in a concentration of from about 30% to about 90%. The semi-fluorinated alkane can be perfluorohexyloctane (F6H8). The atropine can be present in a concentration of from about 0.002% to 0.04% (w/w). The atropine can be in a free base form. The atropine in the topical ophthalmological composition can be chemically stable for at least 1 year. The topical ophthalmological composition can be a non-aqueous solution, a suspension, or an emulsion.

In another embodiment, a topical ophthalmological composition is provided, comprising about 0.001% to about 0.1% (w/w) atropine in free base form as an active pharmaceutical ingredient (API); about 10% to about 70% medium chain triglyceride (MCT) liquid vehicle; and about 30% to about 90% semi-fluorinated alkane compound selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10).

In this and other embodiments, the MCT can be present in a concentration of about 10% and the semi-fluorinated alkane compound can be present in a concentration of about 90%. The atropine can be present in a concentration of from about 0.002% to 0.04%.

The atropine can be in a free base form.

In another embodiment, a method is provided for slowing myopia progression in a subject or for relieving vitreous floater symptoms in a subject, comprising administering a topical ophthalmological composition, comprising about 0.001% to about 0.1% (w/w) atropine as an active pharmaceutical ingredient (API); a medium chain triglyceride (MCT) liquid vehicle; and a semi-fluorinated alkane compound selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10).

In another embodiment, a method is provided for slowing myopia progression in a subject or for relieving vitreous floater symptoms in a subject, comprising administering a topical ophthalmological composition, comprising about 0.001% to about 0.1% (w/w) atropine in free base form as an active pharmaceutical ingredient (API); about 10% to about 70% medium chain triglyceride (MCT) liquid vehicle; and about 30% to about 90% semi-fluorinated alkane compound selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10).

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the chromatogram of Atropine (tR: 12.947) standard solution.

DETAILED DESCRIPTION OF THE ILLUSTRATED EMBODIMENTS

Figure 2:
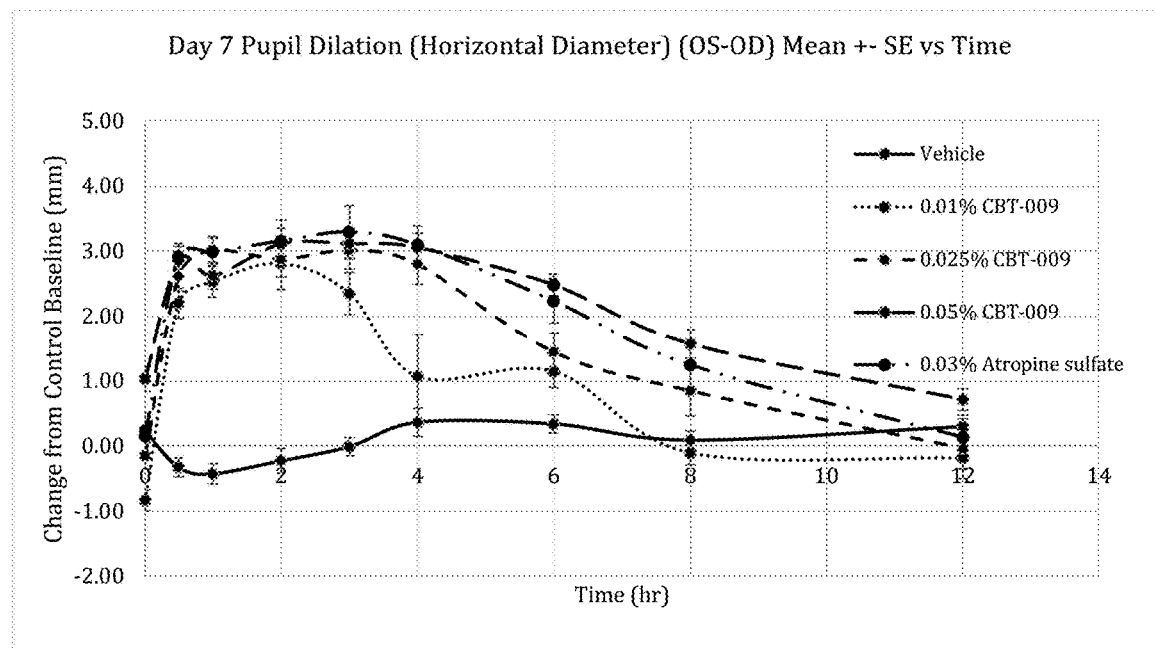
FIG. 2 shows the pupil size measurement at day 7 post dosing of Example 5.

Reference will now be made in detail to embodiments of the present invention, example of which is illustrated in the accompanying drawings.

A muscarinic receptor antagonist is an anticholinergic agent that blocks the activities of a muscarinic acetylcholine receptor. The muscarinic receptor antagonist may be atropine, pirenzepine, aclidinium bromide, benztropine, cyclopentolate, diphenhydramine, doxylamine, dimenhydrinate, dicyclomine, darifenacin, flavoxate, hydroxyzine, ipratropium, mebeverine, oxybutynin, procyclidine, scopolamine, solifenacin, tropicamide, tiotropium, trihexyphenidyl, or tolterodine. Preferably, the muscarinic receptor antagonist is atropine or pirenzepine. More preferably, the muscarinic receptor antagonist is atropine.

Medium-chain triglycerides (MCTs) are triglycerides of fatty acids. The fatty acids have an aliphatic chain of 6-12 carbon atoms, and can be, for example, hexanoic acid, octanoic acid, decanoic acid, and dodecanoic acid. The MCTs can be a single triglyceride or a mixture of triglycerides. Representative chemical structures of the MCTs are shown below.

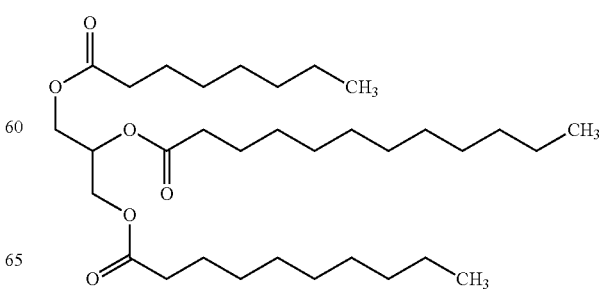

-continued

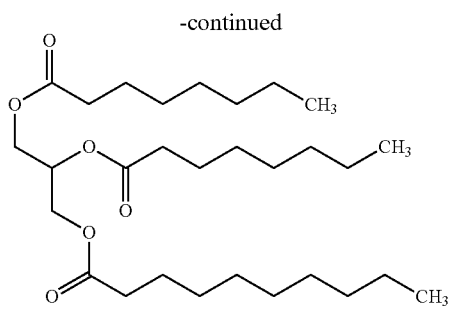

Light liquid paraffin oil (paraffinum liquidum) is a refined mineral oil used in cosmetics and medicine. It contains a mixture of liquid saturated hydrocarbons.

Semifluorinated alkane is an amphiphilic liquid with two mutually immiscible moieties (hydrocarbon segment and perfluorinated segment) bound covalently. Examples of Semifluorinated alkanes include perfluorobutylpentane (F4H5), perfluorobutylhexane (F4H6), perfluorohexylbutane (F6H4), perfluorohexylhexane (F6H6), perfluorohexyloctane (F6H8), and perfluorohexyldecane (F6H10); preferably, perfluorobutylpentane (F4H5), perfluorohexylhexane (F6H6), and perfluorohexyloctane (F6H8).

The structure of F6H8 is shown below.

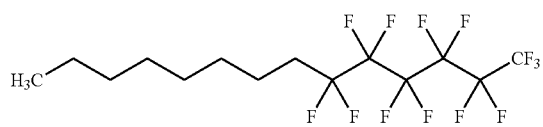 [SMILES: CCCCCCCCC(F)(F)C(F)(F)C(F)(F)C(F)(F)C(F)(F)C(F)(F)F]

F6H8 ($CF_3(CF_2)_5(CH_2)_7CH_3$)

Atropine solution (water) formulations had been previously proven effective in treating myopia, specially reducing myopia progression. The solution formulation had two drawbacks. The first is that once the container opens to air, the atropine at neutral pH in the solution is prone to degradation, therefore, the shelf life of the product at neutral pH is often less than 1 year. Furthermore, this instability of the atropine in the solution requires that the formulation is used within about a month. The second shortcoming is that the low pH, such as in the pH range of 3.5 to 6.0, used to reduce atropine degradation to increase product shelf life, can cause irritation or discomfort to the human eye as reported of adverse events in the patients. The term "about" means in the range of +20% to −20% of a value, +10% to −10% of the value, or +5% to −5% of the value.

This disclosure provides compositions using a MCT or light liquid paraffin oil as the liquid vehicle to dissolve atropine to eliminate the two shortcomings of the solution formulation. The disclosure, shown in the example, demonstrates that these vehicles can dissolve atropine at sufficient concentration ranges to be effective in myopia treatment.

In some embodiments, the disclosure is based on the studies described in the examples that show atropine can be dissolve in MCTs or light liquid paraffin oil at sufficient concentration to have biological efficacy.

In some embodiments, a cosolvent and/or a semifluorinated alkane is added to the formulation. The cosolvent can be, for example, phenethyl alcohol, ethanol, isopropanol, glycerol, propylene glycol, or polyethylene glycol. The cosolvent and semifluorinated alkane increase the solubility of atropine and the stability of the formulation over a long period of time.

EXAMPLES

Example 1: Dissolution of Atropine in Mcts or Light Liquid Paraffin Oil

Methods: Formulations of atropine free base were investigated according to the following procedure:
1. Dissolving Atropine
Added more than 4 mg of atropine powder in 4 mL of study solvent, and the formulation is stirred for 2 days.
2. Preparing HPLC Samples
Centrifuged the formulations above and filtered the supernatants through 0.45 micron filters without further dilution. One sample was prepared from each solvent for HPLC analysis.
3. Analyzing the HPLC Samples
The samples were analyzed using a RP-HPLC method with an Agilent Eclipse Plus C18 HPLC column (150 mm×2.1 mm I.D.) connected with a guard column (12.5 mm×2.1 mm I.D.) and a gradient elution from 100% water to 100% acetonitrile at a flow rate of 0.2 ml/min. The chromatograms were monitored at UV at 220 nm. The atropine peak is at retention time 12.947 as shown in the chromatograph in FIG. 1.

Results

The solubility of atropine free base in MCT or light liquid paraffin oil are shown in Table 1. Atropine free base was determined to be soluble in light liquid paraffin oil at 75 µg/ml (0.0075% w/w). The addition of 0.1% ethanol to light liquid paraffin oil increased the solubility to 82 µg/ml and the addition of 0.25% phenethyl alcohol to light liquid paraffin oil increased the solubility to above 100 µg/ml. Atropine free base was determined to be soluble in MCT at 3100 µg/ml (0.31% w/w). In this particular study, the free base form of atropine was used, while the mono sulfate salt was previously used in the solution formulation approved for myopia usage. The MW of the free base is 83% equivalent to the mono sulfate salt form of atropine solution formulation. The 0.01% atropine mono sulfate salt solution was previously shown effective for myopia treatment in the clinic and was approved in several countries. This 0.01% atropine salt concentration was equivalent to 0.0083% of the free base concentration. The solubility we observed in MCT is well above that needed for efficacy and the concentration in light liquid paraffin is also in the range of efficacy. In the present application, a concentration of the atropine in the free base form can be from about 0.001% to about 0.5% (w/w), or from about 0.001% to about 0.1% (w/w), for example, about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5% or any range thereof.

TABLE 1

Concentrations of Atropine in Formulations of MCT or Light Liquid Paraffin Oil

| Formulation Systems and Preparation Procedures | Measured Conc. (µg/mL) |
|---|---|
| Saturated atropine free base in light paraffin oil | 75 |

TABLE 1-continued

Concentrations of Atropine in Formulations of MCT or Light Liquid Paraffin Oil

| Formulation Systems and Preparation Procedures | Measured Conc. (µg/mL) |
|---|---|
| Saturated atropine free base in paraffin oil with 0.1% ethanol | 82 |
| Atropine free base in paraffin oil with 0.25% phenethyl alcohol | >100 |
| Saturated atropine free base in MCT | 3100 |

Example 2: Miscibility of Semi-Fluorinated Alkane with Mct or Light Liquid Paraffin Oil F6H8, a semi-fluorinated alkane was tested for miscibility with MCT with the ratio of F6H8 to MCT from 1:99 to 99:1. The results showed that F6H8 was miscible with MCT at all ratios. F6H8, a semi-fluorinated alkane was tested for miscibility with light liquid paraffin oil with the ratio of F6H8 to light liquid paraffin oil from 1:99 to 99:1. The results showed that F6H8 was miscible with light liquid paraffin oil at all ratios.

Example 3: Solubility of Atropine in Formulations of Mct and F6H8 with or without Co-Solvent Using the similar formulation preparation and sample analysis methods described in Example 1, the solubilities of atropine in formulations of MCT and F6H8, with or without co-solvent phenethyl alcohol, were determined and the results are summarized in Table 2.

TABLE 2

Solubilities of Atropine in Formulations containing MCT, F6H8 and phenethyl alcohol

| Formulations | Measured Conc. (µg/mL) |
|---|---|
| 10% MCT, 90% F6H8 | 600 |
| 15% MCT, 85% F6H8 | 600 |
| 20% MCT, 80% F6H8 | 600 |
| 50% MCT, 50% F6H8 | 1500 |
| 70% MCT, 30% F6H8 | 3000 |
| 0.25% phenethyl alcohol, 10% MCT, 89.75% F6H8 | 1200 |
| 0.5% phenethyl alcohol, 10% MCT, 89.5% F6H8 | 2500 |
| 100% F6H8 | 133 |

The data showed that atropine dissolved well in the mixture of MCT and F6H8 at various ratio of MCT: F6H8 ranging from 10% MCT and 90% F6H8 to 70% MCT and 30% F6H8. The addition of co-solvent phenethyl alcohol further increased the solubility of atropine in the mixture of MCT and F6H8. Compared to the solubility of atropine in 100% F6H8, the solubility of atropine increased substantially when MCT was added or MCT and co-solvent phenethyl alcohol were added.

Example 4: Stability of Atropine in Formulations of Mct and F6H8 with or without Co-Solvent Using the similar formulation preparation and sample analysis methods described in Example 1, the stability of atropine at room temperature in formulations of MCT and F6H8, with or without co-solvent phenethyl alcohol, were monitored at baseline, 1 month, 2 months and 3 months and the results are summarized in Tables 3-7.

TABLE 3

Stability of Atropine (expressed as Percentage Relative to the Target Dose) in Formulation of 10% MCT, 90% F6H8

| Percentage Relative to the Target Dose | Baseline | 1 month | 2 months | 3 months |
|---|---|---|---|---|
| 0.01% | 102.92% | 102.40% | 100.97% | 100.88% |
| 0.025% | 99.71% | 98.54% | 98.73% | 98.91% |
| 0.04% | 102.68% | 102.80% | 101.81% | 102.10% |
| 0.05% | 101.37% | 101.02% | 101.13% | 100.49% |

TABLE 4

Stability of Atropine (expressed as Percentage Relative to the Target Dose) in Formulation of 15% MCT, 85% F6H8

| Percentage Relative to the Target Dose | Baseline | 1 month | 2 months | 3 months |
|---|---|---|---|---|
| 0.01% | 99.26% | 103.88% | 102.29% | 98.61% |
| 0.025% | 100.86% | 101.14% | 100.68% | 98.79% |
| 0.05% | 98.98% | 99.90% | 101.04% | 97.58% |

TABLE 5

Stability of Atropine ((expressed as Percentage Relative to the Target Dose) in Formulation of 20% MCT, 80% F6H8

| Percentage Relative to the Target Dose | Baseline | 1 month | 2 months | 3 months |
|---|---|---|---|---|
| 0.01% | 98.76% | 99.54% | 99.58% | 99.24% |
| 0.025% | 96.92% | 96.52% | 97.45% | 96.98% |
| 0.05% | 100.25% | 97.45% | 97.16% | 97.23% |

TABLE 6

Stability of Atropine (expressed as Percentage Relative to the Target Dose) in Formulation of 0.25% phenethyl alcohol, 10% MCT, 89.75% F6H8

| Percentage Relative to the Target Dose | Baseline | 1 month | 2 months | 3 months |
|---|---|---|---|---|
| 0.01% | 98.80% | 99.12% | 98.92% | 92.60% |
| 0.025% | 102.49% | 99.72% | 97.74% | 95.27% |
| 0.05% | 106.24% | 99.09% | 97.84% | 93.35% |

TABLE 7

Stability of Atropine (expressed as Percentage Relative to the Target Dose) in Formulation of 0.5% phenethyl alcohol, 10% MCT, 89.5% F6H8

| Percentage Relative to the Target Dose | Baseline | 1 month | 2 months | 3 months |
|---|---|---|---|---|
| 0.01% | 100% | 101.00% | 99.08% | 94.70% |
| 0.025% | 98.95% | 102.25% | 97.84% | 95.68% |
| 0.05% | 98.95% | 100.30% | 98.83% | 95.28% |

Example 5: In Vivo Pharmacological and Ocular Toxicity Study in a Rabbit Model The purpose of this study was to determine the pharmacological potency and the potential ocular toxicity of the atropine formulation in 0.25% phenylethyl alcohol, 10% MCT and 89.75% F6H8. Test articles were administered by topical ocular instillation to New Zealand White rabbits twice daily for 28 days. The pharmacological potency was measured as pupil dilation in normal naïve rabbits. Three concentrations of atropine (0.01%, 0.025%, 0.05%) in the formulation above were compared to that of an aqueous formulation of 0.03% atropine sulphate salt, which was known to have good pupil dilation effects. The formulation without atropine served as the vehicle control in the study.

Study Design:

The study design is shown in Table 8. Forty eight rabbits (24 per sex) were randomly assigned to 5 groups to determine the toxicity of atropine when administered twice daily for 28 days by topical instillation. The control group was administered with vehicle. Animals were randomly assigned to groups based on body weight. The control and high dose group were 6/sex/group, the low, mid dose and comparator group were 4/sex/group. The last surviving animals in the control and high dose groups were allocated for recovery.

Conc.=Concentration M=Male. F=Female

Atropine in vehicle or control article or comparator alone were administered to left eye of animals twice daily with approximately 12 hours apart by topical instillation for 28 days. The right eye remained the untreated control eye. Animals were dosed via topical ocular instillation to the left eyes at a volume of 40 μL/eye.

Various in-life measurement including viability, clinical observations, body weights, food consumption, ophthalmologic examinations, intraocular pressure, electroretinography as well as pharmacologic evaluation of pupil size measurement were conducted in the study. In addition, macroscopic examination of necropsy, gross observations, organ weights measurement and histopathology were conducted at the end of the study. The study followed the Good Laboratory Practice (GLP).

Figure 3:
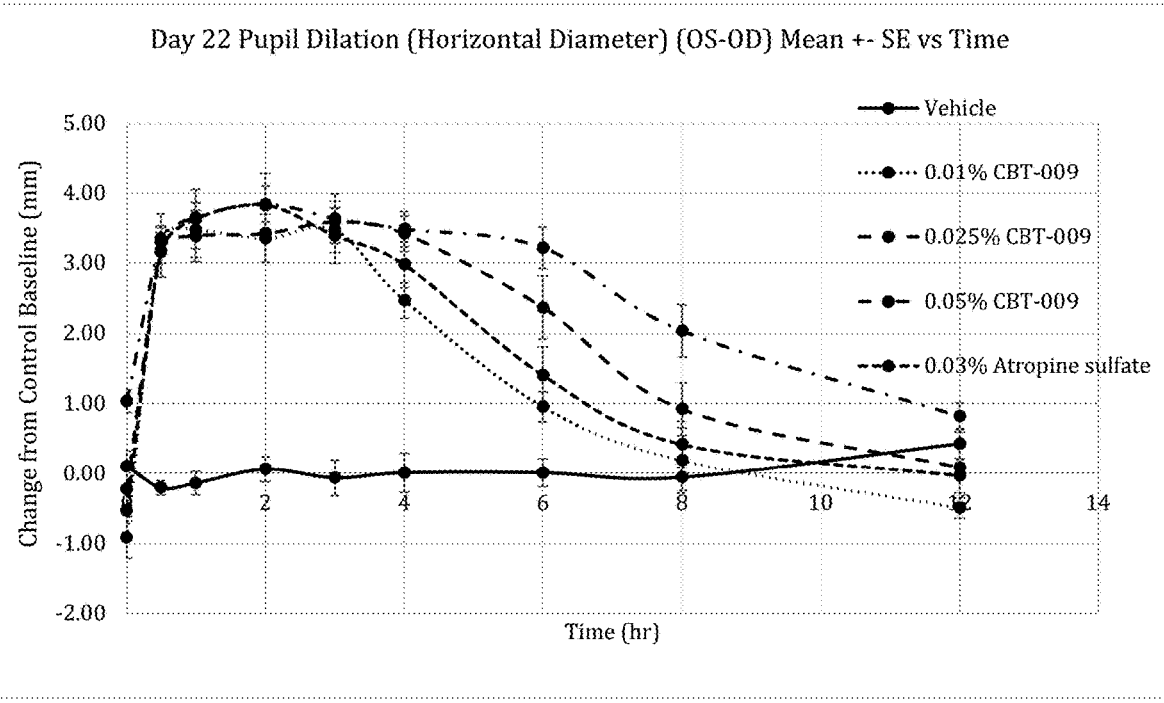
FIG. 3 shows the pupil size measurement at day 22 post dosing of Example 5.

Results:

Pharmacology Assessment: Pupil size were measured in both eyes of all animals on 3 separate days during acclimation prior to dosing initiation to establish the baseline and acclimation of animals to the procedure. The results are shown in FIG. 2 (pupil size measurement at day 7 post dosing) and FIG. 3 (pupil size measurement at day 22 post dosing). The pupil size of both eyes of all animals were measured at baseline (30 minutes before dosing), 0.5 hr, 1 hr, 2 hr, 3 hr, 4 hr, 6 hr, 8 hr and 12 hr after $1^{st}$ dose on $7^{th}$ day and $22^{nd}$ day. CBT-009 represented atropine. The data showed that pupil size dilation was observed in all three dose groups of CBT-009 (atropine) at 0.01%, 0.025% and 0.05% as well as the comparator group of 0.03% atropine sulfate in aqueous formulation while no pupil size change was observed in vehicle-treated group. In addition, dose response in pupil size dilation was observed from 0.01% to 0.05% for atropine at both Day 7 and Day 22 and the magnitude of pupil size changes were comparable between atropine in F6H8-based formulation and atropine sulfate in aqueous solution at comparable doses.

TABLE 8

The Study Design

| Group/ Code color | Test article Designation | Treatment (binocularly) Dose [a] | | | | Numbering of Animals [b] | | | |
|---|---|---|---|---|---|---|---|---|---|
| | | Dose [c] (mg/left eye/day) | No. of Doses/ left eye/day | Volume (μL/left eye) | Conc. (mg/g) | Dosing Phase | | Recovery | |
| | | | | | | M | F | M | F |
| 1 (control)/White | Vehicle | 0 | 2 | 40 | 0 | 1001-1004 | 1501-1504 | 1005-1006 | 1505-1506 |
| 2 (low)/Green | Atropine | 0.008 | 2 | 40 | 0.10 | 2001-2004 | 2501-2504 | — | — |
| 3 (mid)/Yellow | Atropine | 0.020 | 2 | 40 | 0.25 | 3001-3004 | 3501-3504 | — | — |
| 4 (high)/Red | Atropine | 0.040 | 2 | 40 | 0.50 | 4001-4004 | 4501-4504 | 4005-4006 | 4505-4506 |
| 5 (comparator)/ Cyan | Comparator [d] | 0.024 | 2 | 40 | 0.30 | 5001-5004 | 5501-5504 | — | — |

Note:
In this protocol, "dose level" and "dosage" are used interchangeably, "concentration" and "strength" are used interchangeably.
[a] Doses represent active ingredient, left eye will be treated and right eye will be remained untreated
[b] Replacement animals, if any, will be numbered per Testing Facility SOP and will be included in the study report.
[c] Estimated daily dose levels are calculated by the present dosing concentration, volume and frequency.
[d] The comparator is 0.03% atropine sulfate monohydrate in saline containing 100 ppm benzalkonium chloride (BAK).
Conc. = Concentration
M = Male.
F = Female Note: In this protocol, "dose level" and "dosage" are used interchangeably, "concentration" and "strength" are used interchangeably.
[a] Doses represent active ingredient, left eye will be treated and right eye will be remained untreated
[b] Replacement animals, if any, will be numbered per Testing Facility SOP and will be included in the study report.
[c] Estimated daily dose levels are calculated by the present dosing concentration, volume and frequency.
[d] The comparator is 0.03% atropine sulfate monohydrate in saline containing 100 ppm benzalkonium chloride (BAK).

Ocular Toxicity: 0.01%, 0.025% and 0.05% atropine in F6H8f-based formulation, the control vehicle or a comparator of 0.03% atropine sulfate in aqueous solution were administered to the left eyes of male and female New Zealand White rabbits by twice daily topical instillation and the right eyes were untreated. Following the end of the dosing period, terminal-interval animals were euthanized and recovery-interval animals were maintained for a 14-day recovery period and then euthanized. All animals were maintained for a 14-day recovery period and then euthanized. All animals from the terminal and recovery intervals survived to their scheduled euthanasia. No atropine-related macroscopic (gross necropsy) observations or microscopic findings were noted in ocular and non-ocular tissues at either interval. The few microscopic findings in various ocular and non-ocular tissues of control, atropine-treated and/or comparator groups males and females at both intervals were considered incidental and unrelated to atropine. Treatments were tolerated in all study groups and no death was observed in the study.

Example 6: In Vivo Ocular Tolerability Study in a Rabbit Model

Study Design:

Three (3) female Dutch belted rabbits were given 40 μL of 0.012% atropine free base in 100% MCT to the right eyes and 40 μL of 0.012% atropine free base in 100% light liquid paraffin (LLP) to the left eyes, 1 drop/eye, twice per day, 12 hrs apart for 14 consecutive days. Ocular discomfort observation and ocular irritation observation were performed for all animals at predose (twice, on different days) and daily during the dosing phase after the last daily dose. Cornea examination was performed for all animals at predose (once) phase and once after the last daily dose on Day 1 and Day 14. The first dosing day were designated as D1 and the last dosing day was designated as D14.

The ocular irritation results are shown in Table 9 and 10.

The atropine formulation was well tolerated in all rabbits. No significant ocular irritation or ophthalmic findings were observed in any animals. There were no test article-related effects on body weights and food consumption during the study. There were no other test article-related ophthalmologic findings during the scheduled examinations for all animals. No or mild (+1) conjunctiva swelling or conjunctiva congestion was observed during the study. This Example demonstrated the safety of the claimed novel formulation of atropine for ocular use.

Example 7: In Vivo Ocular Tolerability Study in a Dog Model

Study Design

Three (3) male Beagle dogs were given 40 μL of 0.012% atropine free base in 100% MCT to the right eyes and 40 μL of 0.012% atropine free base in 100% LLP to the left eyes, 1 drop/eye, twice per day, 12 hrs apart for 14 consecutive days. Ocular discomfort observation and ocular irritation observation were performed for all animals at predose (twice, on different days) and daily during the dosing phase after the last daily dose. Cornea examination were performed for all animals at predose (once) phase and once after the last daily dose on Day 1 and Day 14. The first dosing day were designated as D1 and the last dosing day was designated as D14.

The ocular irritation results are shown in Tables 11 and 12.

TABLE 9

| | | Slight (+1) Conjunctiva Swelling Incidence (%) (Study Day) | | | | | | | | | | | | | |
|---|---|---|---|---|---|---|---|---|---|---|---|---|---|---|---|
| Group | Eye | D1 | D2 | D3 | D4 | D5 | D6 | D7 | D8 | D9 | D10 | D11 | D12 | D13 | D14 |
| 0.012% in MCT | R | — | — | — | — | — | — | 100% | 33% | 33% | 67% | 67% | 67% | 100% | 100% |
| 0.012% in LLP | L | — | 33% | 33% | 33% | 33% | 33% | 100% | 33% | — | 100% | 100% | 100% | 100% | 100% |

TABLE 10

| | | Slight (+1) Conjunctiva Congestion Incidence (%) (Study Day) | | | | | | | | | | | | | |
|---|---|---|---|---|---|---|---|---|---|---|---|---|---|---|---|
| Group | Eye | D1 | D2 | D3 | D4 | D5 | D6 | D7 | D8 | D9 | D10 | D11 | D12 | D13 | D14 |
| 0.012% in MCT | R | — | — | — | — | — | — | — | 67% | 100% | 100% | 100% | 100% | 67% | 100% |
| 0.012% in LLP | L | — | — | — | — | — | — | 100% | 67% | 100% | 100% | 100% | 100% | 100% | 100% |

TABLE 11

| | | \multicolumn{14}{c}{Slight (+1) Conjunctiva Swelling Incidence (%) (Study Day)} | | | | | | | | | | | | | |
|---|---|---|---|---|---|---|---|---|---|---|---|---|---|---|
| Group | Eye | D1 | D2 | D3 | D4 | D5 | D6 | D7 | D8 | D9 | D10 | D11 | D12 | D13 | D14 |
| 0.012% in MCT | R | — | — | — | — | 67% | — | — | — | — | — | 67% | — | 67% | 100% |
| 0.012% in LLP | L | — | — | — | — | 67% | — | — | — | — | — | 67% | — | 33% | 100% |

TABLE 12

| | | \multicolumn{14}{c}{Slight (+1) Conjunctiva Congestion Incidence (%) (Study Day)} | | | | | | | | | | | | | |
|---|---|---|---|---|---|---|---|---|---|---|---|---|---|---|
| Group | Eye | D1 | D2 | D3 | D4 | D5 | D6 | D7 | D8 | D9 | D10 | D11 | D12 | D13 | D14 |
| 0.012% in MCT | R | — | — | — | — | — | — | — | — | — | — | — | 100% | — | — |
| 0.012% in LLP | L | — | — | — | — | — | — | — | — | — | — | — | 67% | — | — |

The atropine formulation was well tolerated in all dogs. No significant ocular irritation or ophthalmic findings were observed in any animals. There were no test article-related effects on body weights and food consumption during the study. There were no other test article-related ophthalmologic findings during the scheduled examinations for all animals. No or mild (+1) conjunctiva swelling or conjunctiva congestion was observed during the study. This Example demonstrated the safety of the claimed novel formulation of atropine for ocular use.

REFERENCES

1. Berton B, Chennell P, Yessaad M, Bouattour Y, Jouannet M, Wasiak M, Sautou V. Stability of Ophthalmic Atropine Solutions for Child Myopia Control. Pharmaceutics. 2020 Aug. 17; 12(8):E781.
2. Cooper J, Tkatchenko A V. A Review of Current Concepts of the Etiology and Treatment of Myopia. Eye Contact Lens. 2018 July; 44(4):231-247.
3. Li F F, Yam J C. Low-Concentration Atropine Eye Drops for Myopia Progression. Asia Pac J Ophthalmol (Phila). 2019 Sep.-Oct.; 8(5):360-365.
4. Saito J, Imaizumi H, Yamatani A. Physical, chemical, and microbiological stability study of diluted atropine eye drops. J Pharm Health Care Sci. 2019 Dec. 5; 5:25.
5. Wu P C, Chuang M N, Choi J, Chen H, Wu G, Ohno-Matsui K, Jonas J B, Cheung CMG. Update in myopia and treatment strategy of atropine use in myopia control. Eye (Lond). 2019 January; 33(1):3-13.
6. Yam J C, Li F F, Zhang X, Tang S M, Yip B H K, Kam K W, Ko S T, Young A L, Tham C C, Chen L J, Pang C P. Two-Year Clinical Trial of the Low-Concentration Atropine for Myopia Progression (LAMP) Study: Phase 2 Report. Ophthalmology. 2020 July; 127(7):910-919.

What is claimed is:

1. A topical ophthalmological composition comprising:
    about 0.001% to about 0.1% (w/w) atropine as an active pharmaceutical ingredient (API);
    a medium chain triglyceride (MCT) liquid vehicle; and
    a semi-fluorinated alkane compound selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10), wherein the topical ophthalmological composition is non-aqueous.
2. The topical ophthalmological composition of claim 1, wherein the MCT is present in a concentration of from about 10% to about 70% (w/w) and the semi-fluorinated alkane compound is present in a concentration of from about 30% to about 90% (w/w).
3. The topical ophthalmological composition of claim 1, wherein the atropine is present in a concentration of from about 0.002% to 0.04% (w/w).
4. The topical ophthalmological composition of claim 3, wherein the atropine is in a free base form.
5. The topical ophthalmological composition of claim 1, wherein the MCT is a triglyceride of fatty acids selected from the group consisting of hexanoic acid, octanoic acid, decanoic acid, and dodecanoic acid.
6. The topical ophthalmological composition of claim 1, wherein the MCT is present in a concentration of about 10% (w/w) and the semi-fluorinated alkane compound is present in a concentration of about 90% (w/w).
7. The topical composition of claim 1, wherein the semi-fluorinated alkane is perfluorohexyloctane (F6H8).
8. The topical composition of claim 1, wherein the MCT comprises octanoic acid, decanoic acid, or a combination thereof.
9. The topical ophthalmological composition of claim 1, wherein the atropine in the topical ophthalmological composition is chemically stable for at least 1 year.
10. A topical ophthalmological composition comprising:
    about 0.001% to about 0.1% (w/w) atropine in free base form as an active pharmaceutical ingredient (API);
    about 10% to about [70%]50% (w/w) medium chain triglyceride (MCT) liquid vehicle; and
    about [30%]50% to about 90% (w/w) semi-fluorinated alkane compound selected from the group consisting of perfluorobutylheptane (F4H5), perfluorobutylhexane (F4H6), perfluorohexylbutane (F6H4), perfluorohexylhexane (F6H6), perfluorohexyloctane (F6H8), and perfluorohexyl decane (F6H10), wherein the topical ophthalmological composition is non-aqueous.
11. The topical ophthalmological composition of claim 10, wherein the MCT is present in a concentration of about 10% (w/w) and the semi-fluorinated alkane compound is present in a concentration of about 90% (w/w).
12. The topical ophthalmological composition of claim 11, wherein the atropine is present in a concentration of from about 0.002% to 0.04%, and wherein the atropine is in a free base form.

13. A method for slowing myopia progression in a subject or for relieving vitreous floater symptoms in a subject, comprising administering the topical ophthalmological composition of claim 1 to an eye of the subject.

14. A method for slowing myopia progression in a subject or for relieving vitreous floater symptoms in a subject, comprising administering the topical ophthalmological composition of claim 10 to an eye of the subject.

15. The topical ophthalmological composition of claim 10, wherein the MCT is present in a concentration of about 10% to about 20% (w/w) and the semi-fluorinated alkane compound is present in a concentration of about 80% to about 90% (w/w).

* * * * *

UNITED STATES PATENT AND TRADEMARK OFFICE
CERTIFICATE OF CORRECTION

PATENT NO. : 12,070,501 B1
APPLICATION NO. : 17/976660
DATED : August 27, 2024
INVENTOR(S) : Jinsong Ni, Van Dinh and Rong Yang Page 1 of 2

It is certified that error appears in the above-identified patent and that said Letters Patent is hereby corrected as shown below:

On the Title Page

Column 2 (Item (56) under Other Publications), Line 3, Delete "Nr.:7," and insert -- No.:7, --.

Column 2 (Item (56) under Other Publications), Line 8, Delete "Opthalmology" and insert -- Ophthalmology --.

Column 2 (Item (56) under Other Publications), Line 9, Delete "Nr.:9," and insert -- No.:9, --.

In the Specification

Column 2, Lines 41-42, delete "perfluorobutylheptane (F4H5)" and insert -- "perfluorobutylpentane (F4H5)" --.

Column 3, Line 8, delete "perfluorobutylheptane (F4H5)" and insert -- "perfluorobutylpentane (F4H5)" --.

Column 3, Lines 36-37, delete "perfluorobutylheptane (F4H5)" and insert -- "perfluorobutylpentane (F4H5)" --.

Column 3, Lines 53-54, delete "perfluorobutylheptane (F4H5)" and insert -- "perfluorobutylpentane (F4H5)" --.

Column 3, Approximately Lines 66-67, delete "perfluorobutylheptane (F4H5)" and insert -- "perfluorobutylpentane (F4H5)" --.

In the Claims

Column 13, Line 62, in Claim 1, delete "perfluorobutylheptane (F4H5)" and insert -- "perfluorobutylpentane (F4H5)" --.

Signed and Sealed this
Fifteenth Day of July, 2025

Coke Morgan Stewart
*Acting Director of the United States Patent and Trademark Office*

Column 14, Line 51, in Claim 10, after "about" delete "[70%]".

Column 14, Line 53, in Claim 10, after "about" delete "[30%]".

Column 14, Line 55, in Claim 10, delete "perfluorobutylheptane (F4H5)" and insert -- "perfluorobutylpentane (F4H5)" --.